(12) United States Patent
Tokita et al.

(10) Patent No.: US 8,747,079 B2
(45) Date of Patent: Jun. 10, 2014

(54) LIQUID CONVEYING APPARATUS AND LIQUID CONVEYING METHOD USING MICRO-FLUID DEVICE

(75) Inventors: Toshinobu Tokita, Yokohama (JP); Kosuke Fujimoto, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 709 days.

(21) Appl. No.: 12/532,408

(22) PCT Filed: Mar. 28, 2008

(86) PCT No.: PCT/JP2008/056722
§ 371 (c)(1),
(2), (4) Date: Mar. 10, 2010

(87) PCT Pub. No.: WO2008/123591
PCT Pub. Date: Oct. 16, 2008

(65) Prior Publication Data
US 2010/0163129 A1    Jul. 1, 2010

(30) Foreign Application Priority Data
Apr. 3, 2007  (JP) ................. 2007-097491

(51) Int. Cl.
*F04B 43/12*  (2006.01)
(52) U.S. Cl.
USPC ................... 417/413.2; 310/323.06
(58) Field of Classification Search
CPC ............... F04B 43/095; F04B 43/09
USPC ............ 417/413.2; 310/316.01, 317, 328, 310/323.03–323.06
See application file for complete search history.

(56) References Cited

U.S. PATENT DOCUMENTS

| 4,853,578 A | * | 8/1989 | Takahashi et al. ............ 310/315 |
| 5,872,418 A | * | 2/1999 | Wischnewskiy ......... 310/323.06 |
| 6,655,923 B1 | * | 12/2003 | Lisec et al. ..................... 417/92 |
| 6,674,217 B1 | | 1/2004 | Fujimoto |
| 7,129,618 B2 | * | 10/2006 | Fujimoto et al. ......... 310/316.01 |
| 2004/0256951 A1 | | 12/2004 | Fujimoto et al. .............. 310/317 |
| 2008/0240995 A1 | * | 10/2008 | Murakami ................. 422/82.05 |

FOREIGN PATENT DOCUMENTS

JP    2001045774    2/2001

OTHER PUBLICATIONS

International Preliminary Report on Patentability dated Oct. 6, 2009 in corresponding International Application No. PCT/JP2008/056722.
T. Suzuki, et al., "Fast Pulsatile Flow Included in Net Continuous Flow Generated by a Traveling Wave Micropump", The 10th International Conference on Miniaturized Systems for Chemistry and Life Sciences, pp. 131-133, (2006).
N.T. Nguyen, et al., Design and Optimization of an Ultrasonic Flexural Plate Wave Micropump Using Numerical Simulation, Sensors and Actuators A, 1999, vol. 77, pp. 229-236.
T. Suzuki, et al., Development of Valveless Micropump Piezoelectrically Driven by Traveling Wave, Journal of Japan Society of Applied Electromagnetics, 2005, vol. 13, No. 4, pp. 310-315.
PCT International Search Report and Written Opinion of the International Searching Authority, Mailing Date Jun. 24, 2008 in PCT/JP2008/056722.

* cited by examiner

*Primary Examiner* — Christopher Bobish
(74) *Attorney, Agent, or Firm* — Fitzpatrick, Cella, Harper & Scinto

(57) ABSTRACT

An apparatus system for controlling liquid in a fluid channel in a micro-fluid device has an ultrasonic oscillator for conveying liquid. The ultrasonic oscillator oscillates with amplitude modulation. The apparatus system has a holding section for holding the micro-fluid device on the ultrasonic oscillator to allow a micro-fluid device to be removably fitted to it. A liquid conveying method and a liquid conveying unit showing an improved liquid conveying efficiency are provided.

9 Claims, 4 Drawing Sheets

LIQUID CONVEYING APPARATUS AND LIQUID CONVEYING METHOD USING MICRO-FLUID DEVICE

TECHNICAL FIELD

The present invention relates to a micro-fluid device and an apparatus system using the same. The present invention also relates to a liquid conveying method using a micro-fluid device.

BACKGROUND ART

Regions of MEMS (micro electro mechanical systems) technology attracting attention today include bio analyses, environment analyses and chemical syntheses. Micro-fluid devices or so-called μTAS (micro total analysis systems) are known as devices useful for such analyses and syntheses.

A micro-fluid device is formed by providing a substrate, which is typically made of a semiconductor, glass, ceramic or plastic, with a fluid channel therein and a liquid substance that may be a specimen to be analyzed or a material to be used for a chemical synthesis is made to flow there for the analysis or the synthesis, whichever appropriate.

There is a demand for devices that can reduce the consumption of solvents, specimens and reagents and realize a faster reaction speed to exploit the advantages of microscale if compared with conventional analysis methods or batch treatments and for apparatus systems using such devices.

Known liquid conveying methods for micro-fluid devices include those using piezoelectric devices (Takaaki Suzuki et al., The 10th International Conference on Miniaturized Systems for Chemistry and Life Sciences (μTAS2006) vol. 1, pp. 131-133).

FIG. 5 is a schematic cross sectional view of a known arrangement for conveying liquid. In FIG. 5, reference symbol 100 denotes a micro-fluid device. A fluid channel 110 is formed in the inside of the micro-fluid device 100, while a fixed wall 120 and a movable wall 130 are formed as fluid channel walls. The movable wall 130 is provided with a plurality of projections 135 and piezoelectric devices 140 are arranged at the projections 135. The piezoelectric devices 140 oscillate vertically as illustrated in FIG. 5 when the phases of the voltages being applied to the respective piezoelectric devices 140 are shifted temporarily. Then, as a result, a traveling wave is produced on the movable wall 130. The liquid in the fluid channel 110 can be conveyed, while being agitated, by utilizing the traveling wave.

To be more specific, as the movement of the liquid that is found in the fluid channel 110 and driven to move in the x- and y-directions (or three-dimensionally also in the z-direction) as illustrated in FIG. 5 is averaged, the liquid in the fluid channel 110 is driven to move in the direction of the traveling wave as a result. Therefore, the liquid can be conveyed in a desired liquid conveying direction by controlling the voltages being applied to the respective piezoelectric devices 140 so as to produce a traveling wave in the desired liquid conveying direction.

However, the above described known technique is accompanied by the following problems.

With the liquid conveying method using a traveling wave, the liquid is driven to move back and forth along the liquid conveying direction until it is driven to move in the direction of the traveling wave as a result. Thus, the liquid conveying efficiency of this liquid conveying method is not necessarily high. To improve the liquid conveying efficiency, the liquid is preferably driven to move back and forth to a lesser extent.

For this purpose, the piezoelectric devices 140 should be oscillated so as to make the traveling wave proceed with a lower frequency and a greater amplitude. However, it is difficult to do so because the displacement that each piezoelectric device 140 can illustrate is very small.

Additionally, a large number of piezoelectric devices 140 are required to produce a traveling wave. Then, so many signal generators and amplifiers need to be brought in. As a result, the arrangement for handling the micro-fluid device 100 can become large and costly. Furthermore, since the piezoelectric devices 140 are arranged directly in the micro-fluid device 100, the micro-fluid device 100 should carry a high price tag per se.

Finally, the micro-fluid device 100 illustrates large dimensions that reflect the number of the piezoelectric devices 140 arranged therein.

DISCLOSURE OF THE INVENTION

In view of the above-identified problems of the prior art, it is therefore the object of the present invention to provide a compact and less costly liquid conveying apparatus illustrating an improved liquid conveying efficiency and a liquid conveying method using such an apparatus.

According to the present invention, the above object is achieved by providing a liquid conveying apparatus for driving liquid to move in a fluid channel of a micro-fluid device, comprising an oscillator having a plurality of electro-mechanical energy converting devices and a signal generator for applying at least two voltage signals to the oscillator such that the at least two voltage signals are (A) synchronized in terms of frequency and phase and (B) amplitude-modulated at one and the same frequency and in different phases.

Further, according to the present invention, there is provided a liquid conveying method of driving liquid to move in a channel of a micro-fluid device, comprising a step of supplying at least two voltage signals to an oscillator having a plurality of electro-mechanical energy converting devices such that the at least two voltage signals are (A) synchronized in terms of frequency and phase and (B) amplitude-modulated at one and the same frequency and in different phases.

Thus, according to the present invention, liquid can be conveyed highly efficiently. A liquid conveying apparatus according to the present invention is compact and less costly if compared with any known apparatus.

Further features of the present invention will become apparent from the following description of exemplary embodiments with reference to the attached drawings.

BEST MODE FOR CARRYING OUT THE INVENTION

Now, the present invention will be described in greater detail by referring to the accompanying drawings that illustrate embodiments of the invention.

<First Embodiment>

The first embodiment of the present invention will be described below by referring to FIG. 1.

Figure 1:
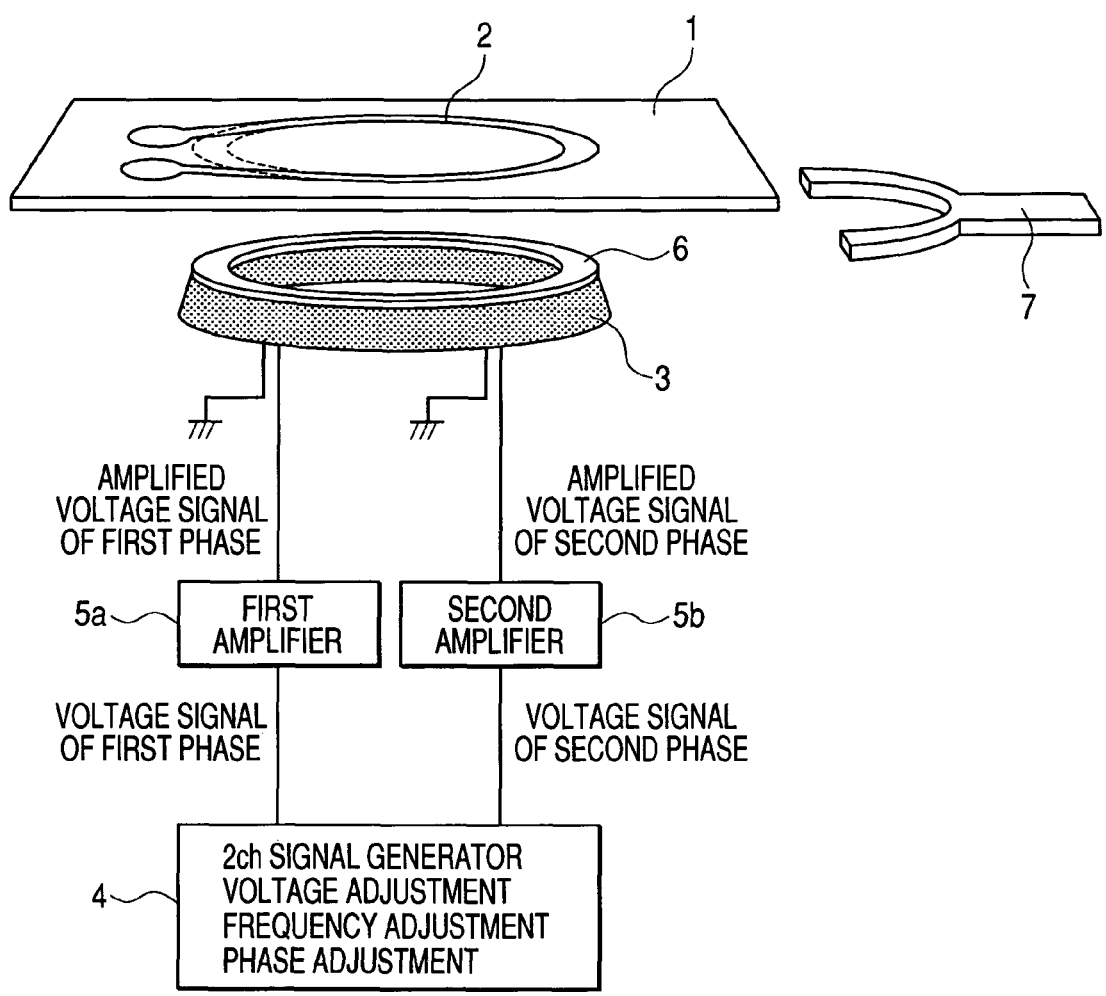
FIG. 1 is a schematic block diagram of the first embodiment.

In FIG. 1, reference symbol 1 denotes a micro-fluid device. The micro-fluid device 1 is provided with a fluid channel 2. A specimen or a reagent is conveyed through the fluid channel 2. At the same time, the specimen or the reagent may be mixed and agitated or the specimen in a solution may be isolated in the fluid channel 2. In FIG. 1, reference symbol 3 denotes an ultrasonic stator that operates as an oscillator having a plurality of electro-mechanical energy converting devices. Typically, an annular stator that can be utilized in an ultrasonic motor may be used for the ultrasonic stator. Reference symbol 4 denotes a signal generator that can generate a voltage signal having a phase, frequency and an amplitude that are variable. Reference symbols 5a and 5b respectively denote a first amplifier 5a and a second amplifier 5b for amplifying the voltage signals generated by the signal generator 4 and applying the voltage signals obtained by amplifying the generated signals to the ultrasonic stator 3 for oscillation. The ultrasonic stator 3 is tightly held in contact with part of the fluid channel 2 of the micro-fluid device 1 by way of a holding section 6. The micro-fluid device 1 may be removably held by the electric oscillator by way of the holding section. Reference symbol 7 denotes a carrier unit for conveying the micro-fluid device 1 to the holding section 6 and collecting the micro-fluid device 1 from the holding section 6.

Normally, the signal generator 4 outputs signals with frequencies that resonate in a state where the ultrasonic stator 3 holds a micro-fluid device 1 by means of the holding section 6 and amplifies the signals by means of the amplifiers 5 to oscillate the ultrasonic stator 3. The ultrasonic stator 3 is a structure equipped with an oscillation source showing two phases and having piezoelectric devices that are electro-mechanical energy converting devices (normally, having a plurality of piezoelectric devices for each phase) and the signal generator 4 outputs signals having respective frequencies that are one and the same relative to each other and phases that are synchronized by way of two channels and the signals of the two channels are amplified respectively by means of the first amplifier 5a and the second amplifier 5b.

Now, the signals that the signal generator 4 generates at the time of conveying liquid will be described below by referring to FIGS. 2A and 2B.

Figure 2A:
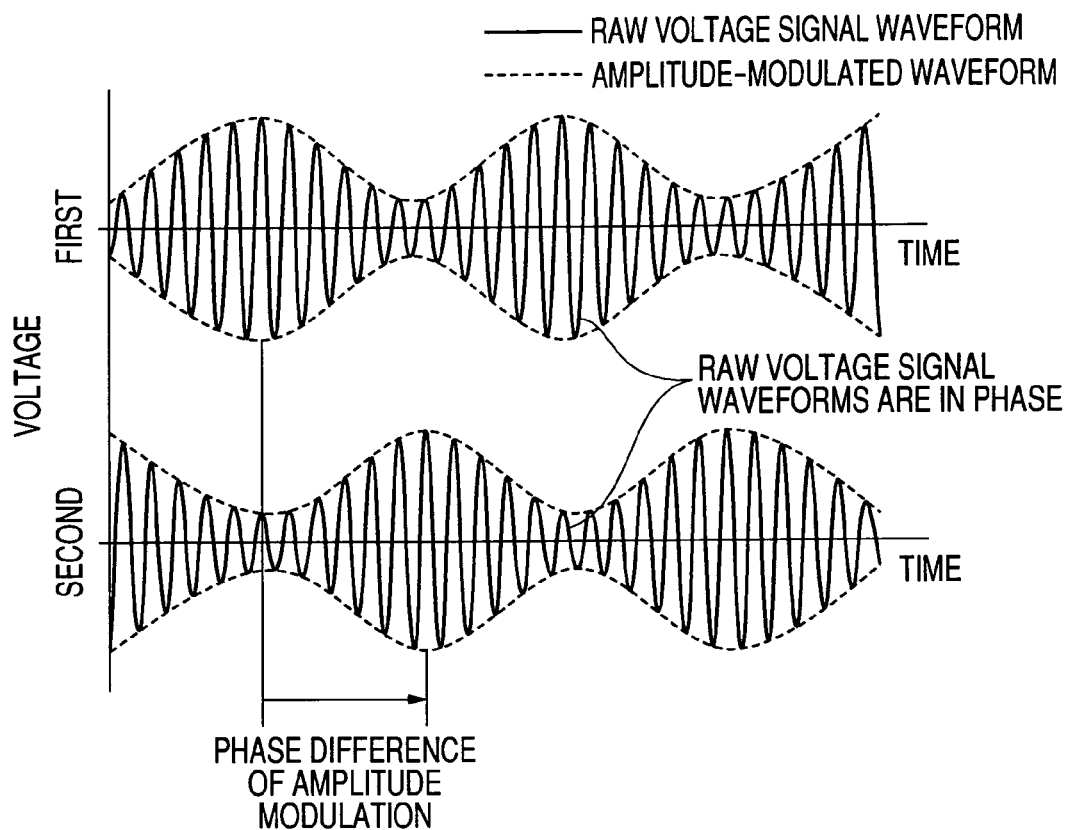
FIGS. 2A and 2B are views illustrating the amplitude modulation and the signal phase relationship of the liquid conveying apparatus of the first embodiment and the deformation of the wall surface of the apparatus.

FIG. 2A illustrates the voltage signal waveforms that the signal generator 4 generates at the time of conveying liquid. The signal generator 4 outputs the signals of the two channels as voltage signals, each of which is subjected to periodical amplitude modulation (AM).

In FIG. 2A, the horizontal axis indicates time and the vertical axis indicates voltage signals. In FIG. 2A, the solid lines show the waveforms of the actual voltage signals while the broken lines show the waveforms of amplitude-modulated voltage signals. As seen from the waveforms of the voltage signals of FIG. 2A, the raw voltage signals of the two channels have respective frequencies that are one and the same relative to each other and phases that are synchronized, whereas the amplitude-modulated voltage signals have phases that are differentiated from each other. FIG. 2A illustrates that the amplitude-modulated voltage signal of the first phase and the amplitude-modulated voltage signal of the second phase show a phase difference of 90°. With this arrangement, the oscillation wave of the ultrasonic stator 3 can turn the standing wave generated by the synchronized two signals into a traveling wave whose displacement of the maximum amplitude moves in a direction. As illustrated in FIG. 2B, the fluid channel walls 2a and 2b that define the wall surfaces of the fluid channel 2 of the micro-fluid device 1 can move the deformation thereof in a predetermined direction with a low frequency that is based on the frequency of the amplitude modulation. As the deformation of the wall surfaces progresses, the liquid in the fluid channel is pushed forward in the traveling direction so that consequently the liquid moves. The lower wall 2b of the fluid channel is held by the ultrasonic stator 3 (not illustrated) by way of the holding section 6. While the upper wall 2a of the fluid channel is illustrated as a fixed wall in FIG. 2B, the present invention is by no means limited thereto and it may alternatively be so arranged that the upper wall 2a is also deformed as oscillation is transmitted to the upper wall 2a from an ultrasonic stator (not illustrated).

Now, how the flow rate or the flow speed of the liquid in the fluid channel is controlled will be described below. The flow rate or the flow speed changes according to the traveling speed and the frequency of the generated traveling wave or the amplitude of the traveling wave.

For the purpose of this embodiment, preferably the frequency of amplitude modulation and the drive voltage (average amplitude) of the traveling wave are adjusted in order to control the traveling speed and the frequency of the traveling wave according to the flow rate or the flow speed required for conveying the liquid. To stop the operation of conveying the liquid, the amplitude may be adjusted so as to become constant when the operation is to be stopped or the supply of the voltage signals may be stopped when the operation is to be stopped.

Preferably, the values of the voltage signals to be supplied to the ultrasonic stator are 10 to 200V and the frequency of the ultrasonic wave signal is 10 to 1 MHz, while the frequency of the amplitude modulation is 10 to 1,000 Hz and the modulation voltage of the amplitude modulation (displacement difference of maximum amplitude) is 10 to 200V, although the present invention is by no means limited thereto.

More preferably, the voltage signal values are 20 to 50V and the frequency of the ultrasonic wave signal is 20 to 100 kHv, while the frequency of the amplitude modulation is 50 to 500 Hz and the modulation voltage of the amplitude modulation is 5 to 50V.

Figure 2B:
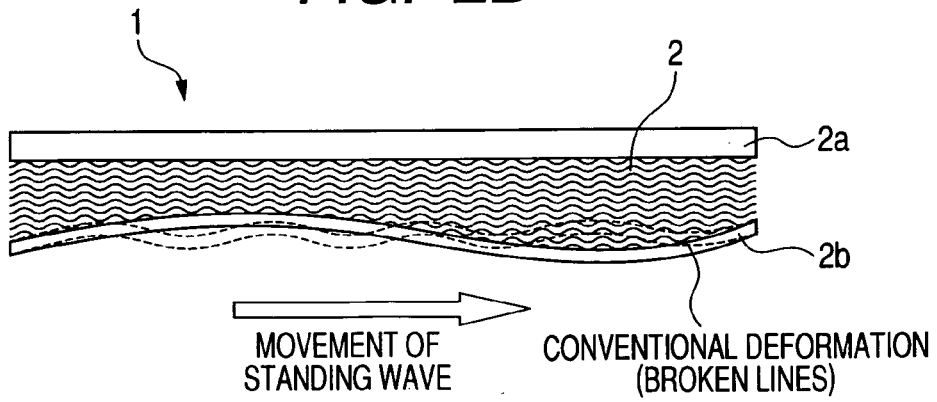

Thus, a standing wave that is deformed to a large extent with an adjusted frequency can be driven to move to improve the liquid conveying efficiency when signals are generated in a manner as illustrated in FIGS. 2A and 2B by means of the arrangement of FIG. 1 as described above.

Further, since liquid can be conveyed by the two-channel signal generator 4, the apparatus system can be made compact and less costly.

The piezoelectric devices that operate as drive source are not required for the micro-fluid device 1 per se when the micro-fluid device 1 is adapted to be removably held by the holding section 6. Then, the micro-fluid device 1 can be downsized and prepared at low cost.

While a two-phase annular stator as illustrated in FIG. 1 is utilized in this embodiment, it may alternatively be a three-phase annular stator. Still alternatively, it may be a linear stator.

U.S. Patent Publication No. 2004/0256951 discloses specific configurations of ultrasonic stator and the present invention can utilize any of the configurations disclosed in the above cited patent document.

The present invention differs remarkably from the prior art ultrasonic motor technology in that the present invention employs two synchronized voltage signals and liquid is driven to move in the traveling direction of a traveling wave.

<Second Embodiment>

Figure 3:
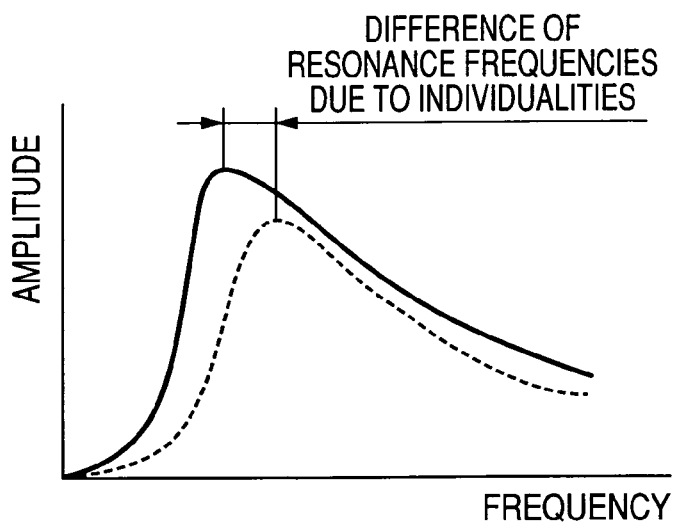
FIG. 3 is a graph illustrating the resonance frequencies.

A liquid conveying method employing amplitude modulation according to the present invention is described for the first embodiment of the invention by referring to FIGS. 1 and 2A and 2B. The signal generator 4 outputs signals with frequencies that resonate in a state where the ultrasonic stator 3 holds a micro-fluid device 1 by means of the holding section 6 as described above for the first embodiment. The resonance frequencies of the signals may vary depending on the individuality of the micro-fluid device 1 as illustrated in FIG. 3 and the condition under which it is held. The second embodiment will be described below in terms of a method of determining the resonance frequencies in a state where the ultrasonic stator 3 holds the micro-fluid device 1 by means of the holding section 6 in order to improve the conveying efficiency by referring to FIG. 4.

Figure 4:
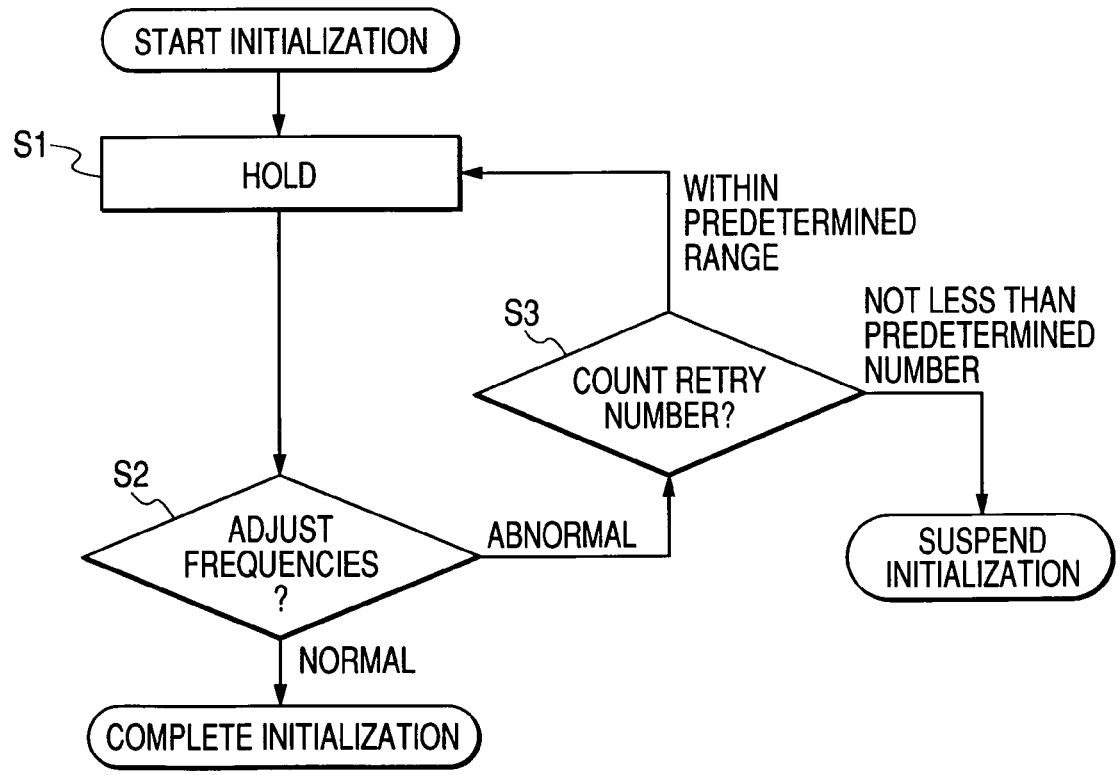
FIG. 4 is a flowchart of the process of initializing the second embodiment.
Figure 5:
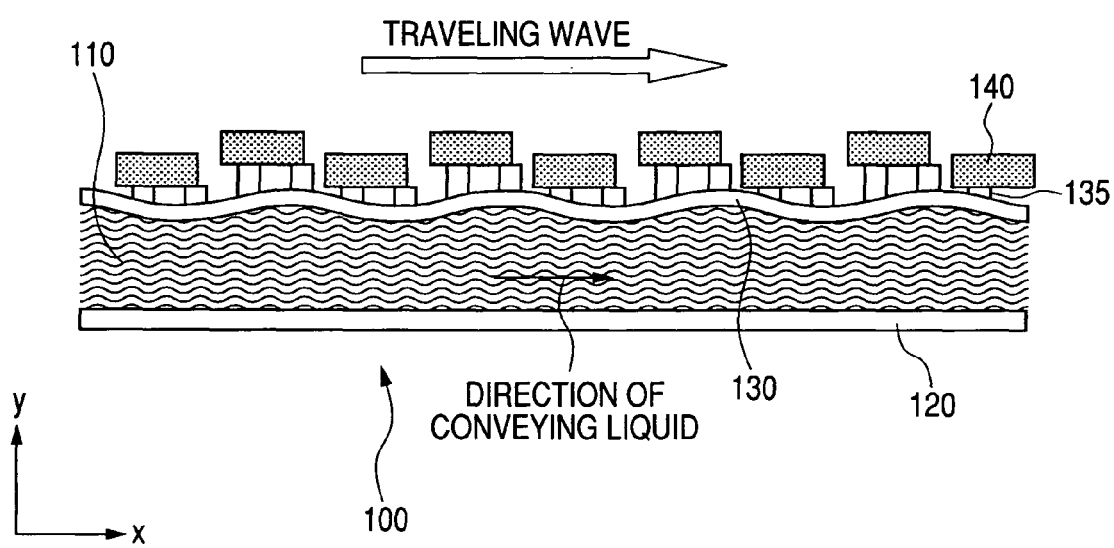
FIG. 5 is a schematic illustration of the prior art.

FIG. 4 is a flowchart of a process of initializing the resonance frequencies. Referring to FIG. 4, S1 denotes the holding step of holding the micro-fluid device 1 by means of the holding section 6. S2 denotes the frequency adjusting step of defining the frequencies of the signals output from the signal generator 4 so as to make them resonate in a state where the ultrasonic stator 3 holds the micro-fluid device 1 by means of the holding section 6. S3 denotes the retry number determining step of counting the number of retries of the holding step S1 and the frequency adjusting step S2 and determining if the retry number is within the defined number or exceeds the defined number. Now, the steps will be described in greater detail below.

S1: Holding Step

The micro-fluid device 1 is conveyed by means of a carrier unit 7 and held by the holding section 6 on the ultrasonic stator 3.

S2: Frequency Adjusting Step

The signal generator outputs sinusoidal waves having a constant amplitude and observes the amplitude of the resonance wave, while changing the frequencies of the sinusoidal waves. The amplitude can be observed by arranging a piezoelectric device for measuring displacements on the ultrasonic stator 3 and seeing the output thereof. Alternatively, a non-contact type displacement meter such as a laser Doppler displacement meter may be arranged to observe the amplitude. The micro-fluid device 1 may be selected as the oscillation observing position or alternatively part of the apparatus system such as the ultrasonic stator 3 or the holding section 6 may be selected as the oscillation observing position. The frequencies that maximize the amplitude are selected as resonance frequencies. Preferably, this step is repeated for a number of times to ensure the reproducibility of the resonance frequencies and the amplitude. A repetition of Step S2 is referred to as retry. The differences of resonance frequencies due to individualities are supposed to be found within a range and hence this step is concluded successfully when the differences are found within such a range. The frequencies of the signals output from the signal generator are defined as resonance frequencies and the initializing step is completed. The next step, or the retry number determining step (S3), is executed when the differences of resonance frequencies due to individualities exceed a predetermined range.

When the differences of resonance frequencies due to individualities exceed a predetermined range, the reproducibility of the resonance frequencies and the amplitude may be ensured and if the differences due to individualities are found within the predetermined range or not may be checked instead of immediately executing the retry number determining step (Step S3).

S3: Retry Number Determining Step

When the resonance frequencies exceed the range that accounts for the differences due to individualities or the reproducibility of the resonance frequencies and the amplitude is poor, the number of times by which the frequency adjusting step (Step S2) was executed is determined. The number of times by which the frequency adjusting step (Step S2) is executed is defined as retry number. The state of the micro-fluid device 1 being held by the holding section 6 and the carrier unit 7 is released when the retry number is less than a predefined number. Then, the process is restarted from the holding step (Step S1). The process is restarted because the micro-fluid device 1 may not have been held properly by the ultrasonic stator 3. If so, the state of the micro-fluid device 1 being held by the ultrasonic stator 3 can be corrected more often than not when the state of the micro-fluid device 1 being held by the ultrasonic stator 3 is released and held anew. However, when the retry number exceeds the predetermined number, the micro-fluid device 1 is highly probably out of order so that the initialization process is suspended because of an over-retry status. Then, the micro-fluid device 1 is collected by the carrier unit 7.

The accuracy of the frequencies selected for resonance is improved in a state where the micro-fluid device 1 is held by the holding section 6 as a result of the above described initialization process so that the liquid conveying efficiency can be improved further. Since the amplitude can be detected when the voltage signals resonate in the frequency adjusting step (Step S2), the flow rate or the flow speed of liquid being conveyed can be controlled by adjusting the output level of the voltage signals.

Now, the present invention will be described further by way of an example that evidences the effect of this invention.

Example 1

An apparatus having a configuration as illustrated in FIG. 1 was prepared in this example. The micro-fluid device of this example was prepared by forming a fluid channel in polymethyl methacrylate (PMMA). The fluid channel had a height of 0.5 mm and a width of 2 mm in cross section and the circular channel showed a diameter of 76 mm as observed between the centers of the cross sections of the fluid channel. Water was introduced by 0.238 ml into the prepared fluid channel. Voltage signals of 30 kHz were synchronized and supplied respectively to the first and second phases to give rise to resonance. Thus, the resonance frequencies could be checked for the arrangement of this example. With the above-described arrangement, resonance frequencies could be defined between 30 and 32 kHz.

A frequency of 100 Hz was selected for amplitude modulation and the flow speed of the water was observed by means of PIV (particle image velocimetry). The speed of the traveling wave produced by the amplitude modulation of 100 Hz was computed to be 2.5 m/s. The input voltage values (Vcc) was set to 40V. As a result, the liquid could be driven to flow at an average flow speed of 10 mm/s.

When first and second 31 kHz traveling waves are applied with an input voltage value of 40V without amplitude modulation, the average flow speed of the liquid was about 1 mm/s so that the effect of amplitude modulation according to the present invention was confirmed.

The present invention is not limited to the above embodiments and various changes and modifications can be made within the spirit and scope of the present invention. Therefore, to apprise the public of the scope of the present invention, the following claims are made.

This application claims the benefit of Japanese Patent Application No. 2007-097491, filed Apr. 3, 2007, which is hereby incorporated by reference herein in its entirety.

The invention claimed is:

1. A liquid conveying apparatus for driving liquid to move in a fluid channel provided in a substrate of a micro-fluid device, the fluid channel having a surface defined by a deformable wall for transmitting vibration to the fluid channel, the apparatus comprising:
 an oscillator having a plurality of electro-mechanical energy converting devices;
 a holding section arranged on the oscillator and connected to the plurality of electro-mechanical energy converting devices, the holding section having a contact surface adapted to be brought into area contact with the deformable wall of the fluid channel such that a holding step is performed in which at least part of the fluid channel of the micro-fluid device is tightly held in contact with the oscillator by way of the holding section;
 a signal generator for applying at least two voltage signals to the oscillator such that the at least two voltage signals are (A) synchronized in terms of frequency and phase and (B) amplitude-modulated at one and the same frequency and in different phases; and
 a frequency adjuster constructed to determine a resonance frequency by outputting a sinusoidal wave showing a constant amplitude and a varied frequency from the signal generator while observing oscillation of the micro fluid device and/or a part of an apparatus system for driving liquid,
 wherein a retry of the determination by the frequency adjuster is repeated for a plurality of times and determination of a resonance frequency is finalized when the determined resonance frequencies and the amplitude are found within a predetermined range, and
 wherein when the determined resonance frequencies and the amplitude exceed the predetermined range, the retry number is counted such that the holding step and a step of counting the retry number are executed again when the retry number is less than a predetermined number whereas when the retry number is not less than the predetermined number the micro-fluid device held by the holding section is collected by means of a carrier unit.

2. The liquid conveying apparatus according to claim 1, further comprising amplifiers for amplifying the at least two signals output from the signal generator.

3. The liquid conveying apparatus according to claim 1, wherein the oscillator is an ultrasonic stator having a two-phase oscillation source for generating ultrasonic standing wave oscillation.

4. A liquid conveying method of driving liquid to move in a fluid channel provided in a substrate of a micro-fluid device, comprising:
 a supplying step of supplying at least two voltage signals to an oscillator having a plurality of electro-mechanical energy converting devices such that the at least two voltage signals are (A) synchronized in terms of frequency and phase and (B) amplitude-modulated at one and the same frequency and in different phases;
 a holding step in which at least part of the fluid channel of the micro-fluid device is tightly held in contact with the oscillator by way of a holding section arranged in contact with the oscillator and connected to the plurality of electro-mechanical energy converting devices; and
 a frequency adjusting step for determining a resonance frequency by outputting a sinusoidal wave showing a constant amplitude and a varied frequency from a signal generator while observing oscillation of the micro-fluid device and/or a part of an apparatus system for driving liquid,
 wherein a retry of the frequency adjusting step is repeated for a plurality of times and determination of a resonance frequency is finalized when the determined resonance frequencies and the amplitude are found within a predetermined range, and
 wherein when the determined resonance frequencies and the amplitude exceed the predetermined range, the retry number is counted such that the holding step and a step of counting the retry number are executed again when the retry number is less than a predetermined number whereas when the retry number is not less than the predetermined number the micro-fluid device held by the holding section is collected by means of a carrier unit.

5. The liquid conveying apparatus according to claim 1, wherein said substrate of a micro-fluid device is made of a semiconductor, glass, ceramic or plastic.

6. The liquid conveying apparatus according to claim 1, wherein a liquid specimen to be analyzed is made to flow through the flow channel for the analysis.

7. The liquid conveying apparatus according to claim 1, wherein said holding section and said substrate are in contact with each other by way of their respective surfaces.

8. The liquid conveying apparatus according to claim 1, wherein the plurality of electro-mechanical energy converting devices are arranged in correspondence to the deformable wall of the fluid channel.

9. The liquid conveying apparatus according to claim 1, wherein the substrate comprises a plate.

* * * * *